United States Patent
Mooney et al.

[11] Patent Number: 6,002,132
[45] Date of Patent: Dec. 14, 1999

[54] THERMIONIC THERMAL DETECTOR AND DETECTOR ARRAY

[75] Inventors: Jonathan M. Mooney, Winchester, Mass.; James E. Murguia, Hollis, N.H.; Prabha K. Tedrow, Lexington, Mass.

[73] Assignee: The United States of America as represented by the Secretary of the Air Force, Washington, D.C.

[21] Appl. No.: 08/958,243

[22] Filed: Oct. 27, 1997

[51] Int. Cl.$^6$ ...................... H01L 31/0328; H01L 31/09
[52] U.S. Cl. .......................... 250/338.4; 257/452
[58] Field of Search ..................... 257/452, 456, 257/455, 454, 451, 449; 250/338.4

[56] References Cited

U.S. PATENT DOCUMENTS

| | | | |
|---|---|---|---|
| 4,203,726 | 5/1980 | Patterson . | |
| 4,544,939 | 10/1985 | Kosonocky et al. | 257/452 |
| 4,922,116 | 5/1990 | Grinberg et al. . | |
| 5,010,251 | 4/1991 | Grinberg et al. . | |
| 5,163,179 | 11/1992 | Pellegrini | 257/451 |
| 5,326,984 | 7/1994 | Rosencher et al. | 257/21 |
| 5,589,688 | 12/1996 | Kimura et al. . | |
| 5,796,155 | 8/1998 | Shepherd et al. | 257/452 |

*Primary Examiner*—Constantine Hannaher
*Attorney, Agent, or Firm*—William G. Auton

[57] ABSTRACT

A new kind of thermal detector and thermal imager for infrared radiation. A thermal detector/imager is a device for detecting/imaging in the infrared portion of the electromagnetic spectrum. This produces a video image, where the video brightness is a function of the incident power. The new thermal imager consists of a thermionic thermal detector having: a substrate having a thermal insulating gap; and a reverse biased $CoSi_2$ diode suspended over the thermal insulating gap of the substrate and which senses temperature of thermionic emission by producing an output signal with a current that changes exponentially with temperature changes. The substrate is a silicon on insulator (SOI) wafer which has said thermal insulating gap on its top surface; an oxide insulator layer that covers the top surface of the thick silicon support layer, including the thermal insulating gap; and support legs placed on the top surface of the oxide insulator layer. The support legs support the reverse biased $CoSi_2$ diode in place.

9 Claims, 2 Drawing Sheets

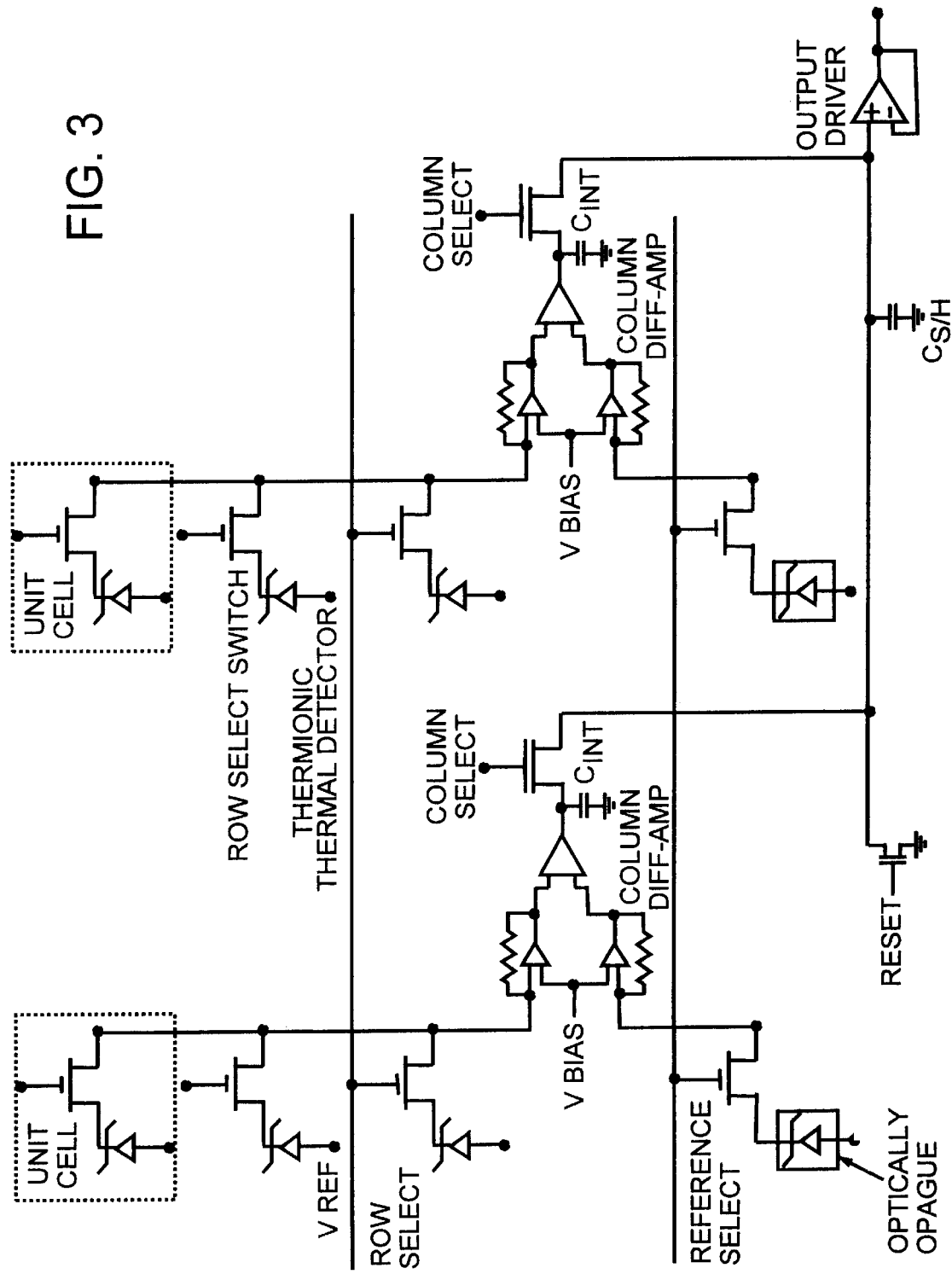

THERMIONIC THERMAL DETECTOR AND DETECTOR ARRAY

CROSS REFERENCE TO RELATED APPLICATION

This application is related to the technology of application Ser. No. 08/502,407 filed on Jul. 14, 1995, the disclosure of which is incorporated herein by reference. This application has been abandoned.

STATEMENT OF GOVERNMENT INTEREST

The invention described herein may be manufactured and used by or for the Government for governmental purposes without the payment of any royalty thereon.

BACKGROUND OF THE INVENTION

The invention relates generally to infrared radiation detectors, and more specifically, it relates to a new kind of thermal detector and imager for high sensitivity thermal imaging.

The themionic thermal detector (TTD) array is similar to both the PtSi Schottky diode infrared detector array that is widely used in the cryogenic infrared community, and vanadium oxide based microbolometer detector array that is widely used in the uncooled infrared community. However, although both the TTD and PtSi detectors are Schottky diodes, the TTD signal detection mechanism is different from that of the PtSi Schottky Infrared detector in that the detector senses temperature via the dark current rather than directly detecting the photoexcited electrons. In addition, the TTD multiplexor is different from that of the PtSi Schottky array. The TTD multiplexor is similar to the vanadium oxide based microbolometer multiplexor, however, the sensing element is a reverse biased diode rather than a resistor.

The task of providing infrared thermal detection using thermionic detector technology is alleviated by the following U.S. Patents, the disclosures of which are incorporated herein by reference:

U.S. Pat. No 5,010,251 issued to Grinberg et al;
U.S. Pat. No 4,922,116 issued to Grinberg et al;
U.S. Pat. No 5,589,688 issued to Kimura et al;
U.S. Pat. No 4,203,726 issued to Patterson;
U.S. Pat. No 4,533,933 issued to Pellegrini et al; and
U.S. Pat. No 5,163,179 issued to Pellegrini.

The first four references disclose alternative thermionic detector arrays that use radiation sensitive bridges. The last two patents disclose Schottky diode detector arrays. Schottky barrier infrared detector arrays have reached an advanced state of development. There is current production of platinum silicide (PtSi) arrays with more than 300,000 detectors and experimental arrays with more than 1,000,000 detectors. The pixel dimensions of these arrays range from 17 $\mu$m to 25 $\mu$m. The infrared photoemission efficiency of detectors has a balancing concern: if the detector current is too high, the detector will heat up and require more cooling, but if the detector current is too low noise will obscure the signal of interest. The Grinberg et al patents represent the best known art, but this system can be improved by a selection of detector metals in conjunction with the anticipated temperature of operation of the detector. Using cobalt disilicide, the detector operation will be optimized for operation at 300 K and $Pd_2$ Si will be better for 250 kelvin with a 0.4 volt barrier height. The present invention is based upon an idea of selection of detector substances based upon the anticipated temperature of the operation.

SUMMARY OF THE INVENTION

The thermionic thermal imager consists of a substrate having a thermal insulating gap; and a $CoSi_2$ diode suspended over the thermal insulating gap of the substrate and which senses temperature by producing an output signal via thermionic emission with a current that changes exponentially with temperature changes. This system can be configured into a TTD array, an infrared lens, drive electronics, a dewar assembly, a camera body, and a video monitor. One novel aspect of the invention is the thermionic thermal detector array, which senses temperature via dark current rather than photoexcited electrons, and which is assembled from thermionic thermal detectors via microelectronic techniques. The other components are similar to those found in other uncooled thermal imagers.

The TTD is a thermal sensing element that converts radiation to thermionic current. Radiation is the emission of photons from a solid body as a result of an elevation in temperature. The thermionic thermal detector array senses temperature via dark current rather than photoexcited electrons.

The conversion is a two step process; first, the radiation is absorbed by the TTD. The absorbed radiation raises the temperature of the TTD. Second, the higher temperature of the TTD changes the thermionic emission current over the reverse biased Schottky barrier. The current is integrated over a sample time and provides an accurate measure of the temperature of the detector. The thermal isolation of the TTD, and the ideality and barrier height of the Schottky diode determine the conversion efficiency of the detector.

The TTD has several advantages over conventional uncooled thermal detectors. Due to the exponential dependence of detector current on temperature, the TTD has more than three times the responsivity of conventional thermal detectors.

Since the TTD is a diode rather than a resistor, it is best modeled as a current source with high parallel resistance and low series resistance. Due to its low series resistance, the TTD will have much less heat dissipation than conventional thermal detectors. Reduced heat dissipation leads to less thermal noise and increased sensitivity.

It is an object of the present invention to provide high sensitivity thermal imaging.

It is another object of the invention to provide a new kind of thermal detector and imaging array using thermionic detector technology.

These objects will become clearer in view of the description provided below.

DESCRIPTION OF THE DRAWINGS

FIG. 3 illustrates an array architecture and multiplexor suitable for the implementation of a TTD imager.

DESCRIPTION OF THE PREFERRED EMBODIMENT

Figure 1:
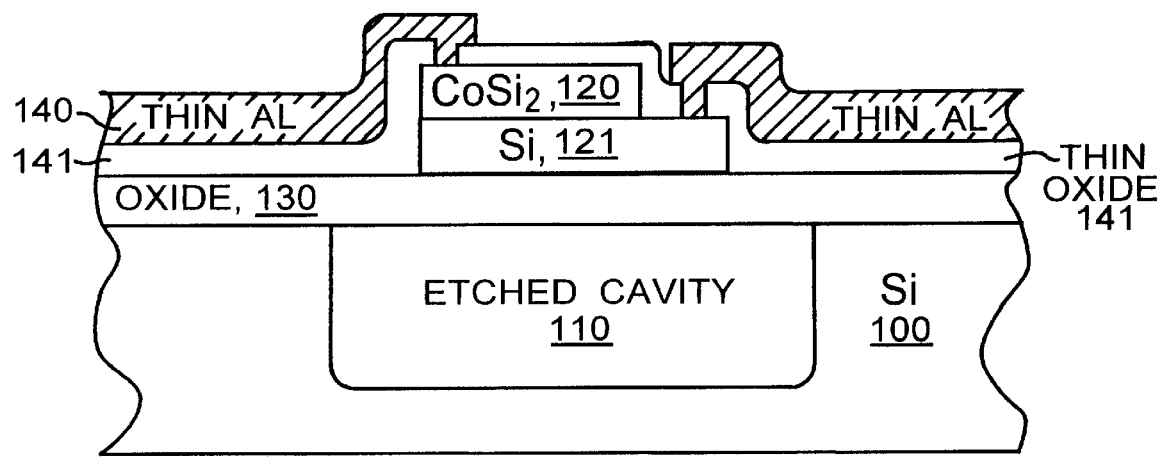
FIGS. 1–2 illustrate a cross section and top down view of a TTD sensing element fabricated on a silicon on insulator (SOI) substrate.

Referring to FIG. 1 of the drawings, there is shown a pictorial representation of the basic elements of a thermionic thermal imager. As shown, it consists of a TTD diode containing: a substrate 100 having a thermal insulating gap 110; and a $CoSi_2$ diode 120 suspended over the thermal insulating gap 110 of the substrate 100 and which senses temperature of thermionic emission by producing an output signal with a current that changes exponentially with temperature changes. The substrate 100 comprises a silicon on insulator (SOI) wafer that contains: a thick silicon support layer 100 which has the thermal insulating gap 110 on its top surface; an oxide insulator layer 130 that covers the top surface of the thick silicon support layer 100; and the bottom surface of the support legs 140 and 141. The legs support the TTD diode in place. The TTD diode includes a silicon electrode 121 and a metallic $CoSi_2$ photoemissive element 120.

The support legs 140 and 141 include: a first and second metallic contact 140, the first metallic contact is electrically connected with said $CoSi_2$ photoemissive element 120, and the second metallic contact is electrically connected with silicon electrode 121. Oxide insulator 130 provides mechanical support and insulation from the silicon substrate.

Figure 2:
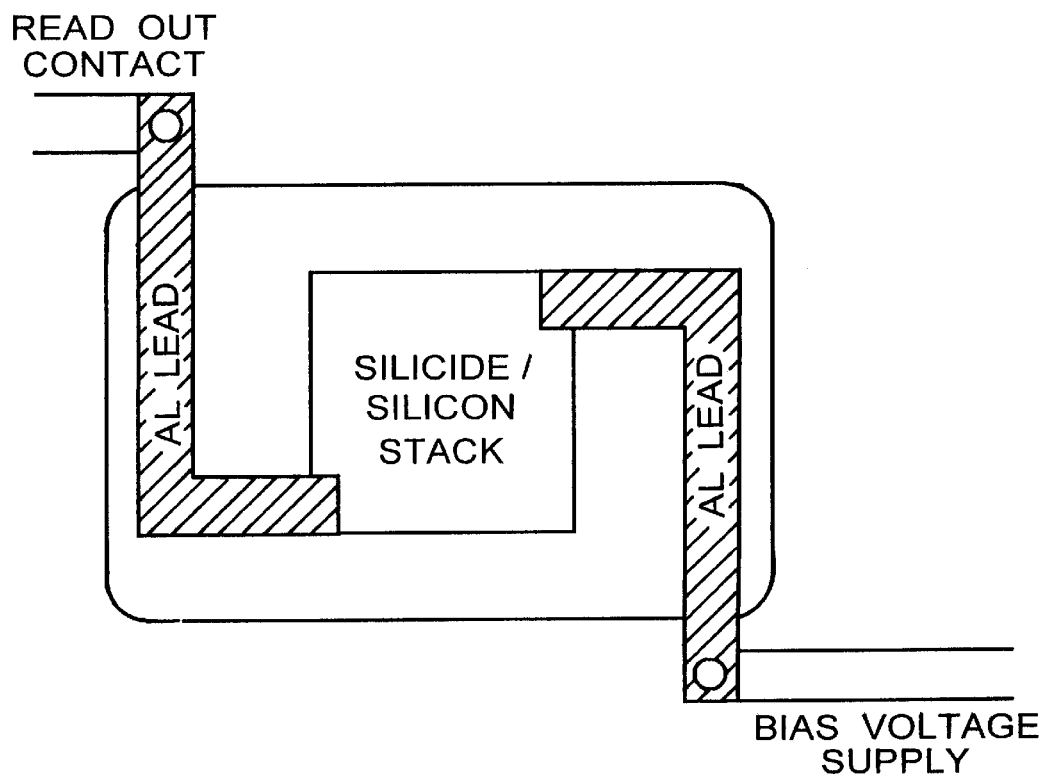

The thermionic thermal detector, as defined in FIG. 1, can use a metallic photoemissive element comprised of materials selected from the group consisting of: $Pd_2Si$, $NiSi_2$, NiSi, $CoSi_2$, CoSi, CrSi, RhSi, $TaSi_2$, $TiSi_2$, $WSi_2$, and $ZrSi_2$, and the invention can be configured as a camera for sensing infrared electromagnetic radiation (emr) comprising: a lens; a substrate having an evacuated chamber; and a focal plane array of thermally insulated Schottky diodes which are suspended over said evacuated chamber of said substrate, and which senses temperature of thermionic emission by producing an output signal with a current that changes exponentially with temperature changes. The elements of this configuration would include: an array, an infrared lens, drive electronics, a dewar assembly, a camera body, and a video monitor. FIGS. 1–2 illustrate a cross section and top down view of a TTD sensing element fabricated on a silicon on insulator (SOI) substrate.

The invention is a new kind of thermal detector and thermal imager for infrared radiation. A thermal detector/imager is a device for detecting/imaging in the infrared portion of the electromagnetic spectrum. This invention produces a video image, where the video brightness is a function of the incident power.

The new thermal imager consists of a thermionic thermal detector/detector array, an infrared lens, drive electronics, an evacuated dewar, a camera body and a video display. The lens, electronics, dewar, camera body and display are all previously demonstrated art. The thermionic thermal detector/detector array is an improvement of the design of Schottky barrier infrared detector (SBIR) arrays.

Referring to FIG. 2 of the drawings, there is shown a pictorial representation of a top down view of the TTD sensing element of FIG. 1 fabricated on a SOI substrate.

Referring to FIG. 3 of the drawings, there is shown a pictorial representation of the array architecture and multiplexor suitable for the implementation of a TTD imager.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A thermionic thermal detector comprising:

a substrate having a thermal insulating gap; and a reverse biased $CoSi_2$ diode suspended over the thermal insulating gap of the substrate and which senses temperature of thermionic emission by producing an output signal with a current that changes exponentially with temperature changes.

2. A thermionic thermal detector, as defined in claim 1, wherein the substrate comprises a silicon on insulator (SOI) wafer.

3. A thermionic thermal detector, as defined in claim 2, wherein the silicon on insulator wafer comprises:

a thick silicon support layer which has said thermal insulating gap on its top surface;

an oxide insulator layer that covers the top surface of the thick silicon support layer, including said thermal insulating gap; and support legs placed on the top surface of the oxide insulator layer, said support legs supporting said $CoSi_2$ diode in place.

4. A thermionic thermal detector, as defined in claim 3, wherein said $CoSi_2$ diode comprises a silicon substrate and a metallic $CoSi_2$ photoemissive element.

5. A thermionic thermal detector, as defined in claim 4, wherein said support legs comprise:

a first and second metallic contact, said first metallic contact being electrically connected with said $CoSi_2$ photoemissive element, and said second metallic contact being electrically connected with said silicon substrate; and a first and second oxide insulator that provides mechanical support and insulation for said silicon substrate.

6. A thermionic thermal detector, as defined in claim 1, wherein said substrate comprises a silicon wafer.

7. A thermionic thermal detector comprising:

a silicon on insulator (SOI) wafer substrate having a thermal insulating gap; and a diode suspended over the thermal insulating gap of the substrate and which senses temperature of thermionic emission with an output current that changes exponentially with temperature changes.

8. A thermionic thermal detector, as defined in claim 1, wherein the diode comprises;

a silicon substrate; and a metallic photoemissive element comprised of materials selected from the group consisting of: $Pd_2Si$, $NiSi_2$, NiSi, $CoSi_2$, CoSi, CrSi, RhSi, $TaSi_2$, $TiSi_2$, $WSi_2$, and $ZrSi_2$.

9. A thermionic thermal detector, as defined in claim 8, wherein the silicon on insulator wafer comprises:

a thick silicon support layer which has said thermal insulating gap on its top surface;

an oxide insulator layer that covers the top surface of the thick silicon support layer, including said thermal insulating gap; and support legs placed on the top surface of the oxide insulator layer, said support legs supporting said $CoSi_2$ diode in place.

* * * * *